United States Patent [19]

Wallace

[11] Patent Number: 5,296,349
[45] Date of Patent: Mar. 22, 1994

[54] MOLECULAR GENETIC TEST FOR MYOCLONIC EPILEPSY
[75] Inventor: Douglas C. Wallace, Atlanta, Ga.
[73] Assignee: Emory University, Atlanta, Ga.
[21] Appl. No.: 538,267
[22] Filed: Jun. 14, 1990
[51] Int. Cl.$^5$ ............................................. C12Q 1/68
[52] U.S. Cl. ........................................ 435/6; 436/811; 536/24.31; 935/78
[58] Field of Search .................. 435/6, 91, 172.3; 436/501, 811; 536/27, 24, 31; 935/78
[56] References Cited

U.S. PATENT DOCUMENTS 4,358,535 11/1982 Falkow et al. ............................ 435/5
4,683,202 7/1987 Mullis ..................................... 435/91

OTHER PUBLICATIONS

Wallace, "Human Genetic Disease Review," Jan. 1989, vol. 5, No. 1.
Saiki et al, Nature vol. 324, 13 (Nov. 1986), pp. 163-166.
Shoffner and Wallace, "Oxidative Phosphorylation Diseases," *Advances in Human Genetics Chapter 5:* 266-330, Harris and Hirschhorn, eds. (1990).
Shoffner et al., "Spontaneous Kearns-Sayre/chronic external ophthalmoplegia plus syndrome associated with a mitochondrial DNA deletion: A slip-replication model and metabolic therapy," *Proc. Natl. Acad. Sci. USA* 86:7952-7956 (1989).
Trounce et al., "Decline in Skeletal Muscle Mitochondrial Respiratory Chain Function: Possible Factor in Ageing," *The Lancet* 637-639 (1989).
Howell and Lee, "Sequence Analysis of Mouse Mitochondrial Chloramphenicol-Resistant Mutants," *Somatic Cell and Molecular Genetics* 15:237-244 (1989).
Wallace et al., "Mitochondrial DNA Mutation Associated with Leber's Hereditary Optic Neuropathy," *Science* 242:1427-1430 (1988).
Innis et al., "DNA sequencing with *Thermus aquaticus* DNA polymerase and direct sequencing of polymerase chain reaction-amplified DNA," *Proc. Natl. Acad. Sci. USA* 85:9436-9440 (1988).
Wallace et al., "Familial Mitochondrial Encephalomyopathy (MERRF): Genetic, Pathophysiological, and Biochemical Characterization of a Mitochondrial DNA Disease," *Cell* 5:601-610 (1988).
Farr et al., "Analysis of *RAS* gene mutations in acute myeloid leukemia by polymerase chain reaction and oligonucleotide probes," *Proc. Natl. Acad. Sci. USA* 85:1629-1633 (1988).
Chomyn et al, "URF6, Last Unidentified Reading Frame of Human mtDNA, Codes for an NADH Dehydrogenase Subunit," *Science* 234:614-234 (1986).
Wallace, "Mitotic Segregation of Mitochondrial DNAs in Human Cell Hybrids and Expression of Chloramphenicol Resistance," *Somatic Cell and Molecular Genetics* 12:41-40 (1986).
Rosing et al., "Maternally Inherited Mitochondrial Myopathy and Myoclonic Epilepsy," *Ann. Neurol.* 17:228-237 (1985).
Wallace, "Cytoplasmic Inheritance of Chloramphenicol Resistance in Mammalian Cells," *Techniques in Somatic Cell Genetics* 159-187, J. W. Shy, ed. (1982).
Anderson et al., "Complete Sequence of Bovine Mitochondrial DNA, Conserved Features of the Mammalian Mitochondrial Genome," *J. Mol. Biol.* 156:683-717 (1982).
Bibb et al., "Sequence and Gene Organization of Mouse Mitochondrial DNA," *Cell* 26:167-180 (1981).
Anderson et al., "Sequence and organization of the human mitochondrial genome," *Nature* 290:457-465 (1981).
Gusella et al., "A polymorphic DNA marker genetically liked to Huntington's disease," *Nature* 306:234-238 (1983).
Laird, Charles D., "Proposed genetic basis of Huntington's Disease," *Trends in Genetics* 6:242-247 (1990).

*Primary Examiner*—Amelia Burgess Varbrough
*Attorney, Agent, or Firm*—Needle & Rosenberg

[57] ABSTRACT

The present invention relates to a method and manufacture for detecting neuromuscular disease, particularly Myoclonic Epilepsy and Ragged Red Fiber disease, by ascertaining whether a transition mutation has occurred at the 8344 nucleotide position in the mitochondrial DNA of a patient. The invention provides methods to detect this mutation including digestion of the patient's mtDNA with restriction endonucleases followed by analysis of the resulting fragments, differential hybridization of oligonucleotides, direct PCR sequencing and denaturing gradient gel electrophoresis.

25 Claims, 4 Drawing Sheets

MOLECULAR GENETIC TEST FOR MYOCLONIC EPILEPSY

ACKNOWLEDGEMENT

The invention described herein was made with Government support under grant no. NS21328 awarded by the National Institutes of Health. The Government has certain rights in this invention.

BACKGROUND OF THE INVENTION

The present invention relates to a method of detecting neuromuscular disease in a patient, particularly Myoclonic Epilepsy and Ragged-Red Fiber disease (MERRF). More particularly, the invention relates to the detection of an adenine to guanidine transition mutation at nucleotide pair (np) 8344 in the human mitochondrial DNA (mtDNA), which alters the TΨC loop of the tRNA$^{Lys}$ gene.

MERRF is a disease associated with uncontrolled myoclonic jerking and skeletal muscle deterioration involving accumulation of mitochondria in muscle cells, which stain red with Gomori modified trichrome and exhibit abnormal mitochondrial structures. The symptoms of the disease vary from mild central nervous system disturbances to deafness, status epilepticus, dementia, cardiomyopathy and respiratory failure.

MERRF has been shown to fulfill all of the criteria for a mitochondrial DNA (mtDNA) mutation. The disease is maternally inherited as is the mtDNA. MERRF is associated with defects in the mitochondrial oxidative phosphorylation (OXPHOS) Complexes I and IV whereas mtDNA encodes Complex I and IV subunits. The severity of the patient's skeletal muscle OXPHOS defect varies along the maternal lineage, consistent with the segregation of a heteroplasmic (mixed mutant and wild type) mtDNA mutation. Finally, as the patient's mitochondrial ATP generating capacity declines, tissues of the central nervous system, skeletal muscle and heart are progressively affected indicating that tissue-specific energetic thresholds are being traversed. However, detailed restriction analysis of MERRF mtDNA has failed to reveal any evidence of insertion-deletion or rearrangement mutations (Wallace et al., *Cell*, 55:601–610 (1988)). Hence, MERRF must be the product of a heteroplasmic mtDNa point mutation.

The mtDNA codes for 7 subunits (NDI, 2, 3, 4L, 4, 5, 6) of respiratory Complex I (NAHD:ubiquinone oxidoreductase), 3 subunits (COI, II and III) of Complex IV (cytochrome c oxidase), 2 subunits (ATPase 6 and 8) of Complex V (ATP synthase) and one subunit (cyt b) of Complex III (ubiquinol:cytochrome c oxidoreductase). In addition, the mtDNA encodes a large and small rRNA gene and a set of 22 tRNAs, including a single tRNA$^{Lys}$, which recognizes the codons AAA and AAG (Anderson et al., *Nature*, 290:457–465 (1981); Shoffner and Wallace, *Advances in Human Genetics*, 19:267–330 (1990)). The 13 mtDNA polypeptides are translated on chloramphenicol-sensitive mitochondrial ribosomes and can be differentially labeled by incubating cells in medium containing $^{35}$S-methionine plus the cytosolic ribosome inhibitor emetine. All the mitochondrial translation products have been assigned to mtDNA genes, and the largest and most numerous of these are subunits of Complexes I and IV (Wallace et al., *Am. J. Hum. Genet.*, 38:461–481 (1986); Chomyn et al., *Science*, 234:614–618 (1986)). In cultured cells, mutations in the mitochondrial large rRNA gene have been isolated which impart chloramphenicol resistance (Wallace, "Cytoplasmic Inheritance of Chloramphenicol Resistance in Mammalian Cells", *Techniques in Somatic Cell Genetics*, 159–187, Plenum Publ. Corp., New York (1982); Howell and Lee, *Somat. Cell Molec. Genet.*, 15:237–244 (1989)). These mutations can result in reduced activity of respiratory complexes, especially Complex I (Howell and Nalty, *Somat. Cell Molec. Genet.*, 14:185–193 (1988)), presumably due to decreased mitochondrial translation.

Analysis of the mitochondrial translation products of lymphoblastoid cell lines derived from MERRF patients have revealed a reduction in the labeling of the high molecular weight polypeptides relative to the smaller polypeptides (Wallace, et al., "Maternally Inherited Diseases of Man", *Achievements and Perspective of Mitochondrial Research, Vol. 2*, Elsevier Science Publishing, New York (1986)). This analysis has led to the speculation that MERRF may be the product of a mutation in a mtDNA, rRNA or tRNA gene.

Therefore, there exists a need to establish the molecular cause of MERRF. Prior to this invention, no method was known for the molecular diagnosis of MERRF or associated diseases. Also, there exists a need to provide a specific molecular test to accurately diagnose the presence of or susceptibility to the disease in a patient.

SUMMARY OF THE INVENTION

The present invention relates to the discovery of an adenine to guanine transition mutation at np 8344 in human mtDNA, which has been identified as the cause of MERRF. This mutation alters the TΨC loop of the tRNA$^{Lys}$ gene and creates a CviJI restriction site, thus providing a simple molecular diagnostic test for the disease.

A survey of restriction-fragment-length polymorphisms in the mtDNA of afflicted and non-afflicted individuals revealed that the mutation was present in three independent MERRF pedigrees and absent in 75 controls. Furthermore, this mutation is heteroplasmic and, in one pedigree, correlated with the clinical, physiological and biochemical abnormalities. This MERRF mutation provides the first evidence that a genetic disease can be caused by a defect in protein synthesis and confirms that some forms of epilepsy are the result of deficiencies in mitochondrial energy production.

The present invention provides a method for detecting MERRF and associated neuromuscular diseases in a patient by testing the mtDNA obtained from any cell of a patient for the presence of a transition mutation at the mtDNA np 8344. The mutation is readily detected in purified mtDNA or in polymerase chain reaction (PCR) amplified fragments by digestion of the patient's mtDNA with a restriction endonuclease, such as CviJI, that differentially cleaves the mutant and wild type mtDNA surrounding np 8344. Alternatively, the presence of the transition mutation is detected by differential hybridization of oligonucleotides with the mutant and wild type mtDNA, use of denaturing gradient gel electrophoresis, or direct PCR sequencing.

More particularly, all or part of the patient's mtDNA can be digested with a restriction endonuclease, such as CviJI, followed by analysis of the resulting fragments to determine the percentage of mtDNA that is cut at np 8344. If the mtDNA is cut at this site, the mtDNA is mutant and possesses the disease causing mutation; it not, the mtDNA is the normal wild type. The cutting of the DNA at this site can be assessed by appropriate procedures such as separating the DNA fragments by agarose electrophoresis followed by Southern blotting, end-labeling the fragments followed by polyacrylamide gel electrophoresis, or amplification of purified, crude, or enriched mtDNA samples preceding the digestion by endonuclease and separation of the digested products on agarose or polyacrylamide gels. The proportion of mutant and wild type mtDNAs can then be determined, using means such as densitometry, and used to predict the degree of clinical, physiological and biochemical abnormalities.

The presence of a transition mutation at np 8344 can also be detected by the differential hybridization of oligonucleotides. Oligonucleotide probes are constructed that are complementary to the nucleotide sequence on one strand surrounding np 8344 for either normal mtDNA or mutant mtDNA. A probe that is complementary to the mutant strand hybridizes with a patient's mtDNA only if the patient possesses the np 8344 mutation. Conversely, a probe that is complementary to the normal strand hybridizes with a patient's mtDNA only if the patient does not possess the disease causing mutation. Thus, the extent of hybridization defines whether the patient possesses the disease causing mutation.

Furthermore, an appropriate fragment of the patient's mtDNA that surrounds the np 8344 position can be amplified using polymerase chain reaction (PCR) techniques and directly sequenced to determine the presence or absence of the mutation, using the dideoxy chain termination procedure or chemical cleavage procedure, resolution of the fragments on on a DNA sequencing gel and detection of the mutation by autoradiography.

In addition, the mutation could be detected using denaturing gradient gels. Restriction endonuclease fragments or PCR fragments surrounding the mutation can be resolved on a polyacrylamide gel containing gradients of denaturants, such as increasing temperature, increasing formamide, urea, and the like. The mutant and normal fragments will denature at different positions in the gel leading to altered migration distances. The resolved fragments can then be detected by DNA hybridization for restriction fragments or direct DNA staining for PCR fragments.

Accordingly, one of the objectives of this invention is to provide a method of detecting neuromuscular disease, particularly MERRF, in a patient. A further object of this invention is to provide a method to test any cell of a patient for the presence of a transition mutation at np 8344 in the patient's mtDNA.

Furthermore, this invention provides a method to assay whether a transition mutation exists at np 8344 of a patient's mtDNA by digesting a sample of the patient's mtDNA with a restriction endonuclease that differentially cleaves mutant and wild type mtDNA followed by determining the length of the resulting mtDNA fragments. The patient's mtDNA sample can contain either complete or partial mtDNA and may be either crude, purified, or amplified mtDNA.

Still further, this invention provides a differential oligonucleotide hybridization method for assaying whether a transition mutation exists at np 8344. This method involves hybridizing a sample of the patient's mtDNA with oligonucleotide probes that are complementary to either normal, wild type mtDNA or mutant mtDNA in the region surrounding np 8344. The patient's mtDNA sample can contain either complete or partial mtDNA and may be either crude, purified, or amplified mtDNA.

Further, this invention provides a method to assay for this point mutation by PCR amplification of the surrounding mtDNA and direct sequencing of the DNA. Additionally, the mutation can be detected by separation of restriction endonuclease or PCR fragments containing the mutation on denaturing gradient gels and detecting the mutant fragment by its altered mobility.

These and other objects and advantages of the present invention are apparent to a person skilled in the art from the following detailed description, which is not intended to be limiting.

DETAILED DESCRIPTION OF THE INVENTION

1. Identification of the np 8344 Mutation as the Cause of MERRF

As used herein, amplified DNA refers to DNA that has been reproduced using a PCR technique; enriched DNA refers to a DNA sample that has been concentrated.

Figure 1:
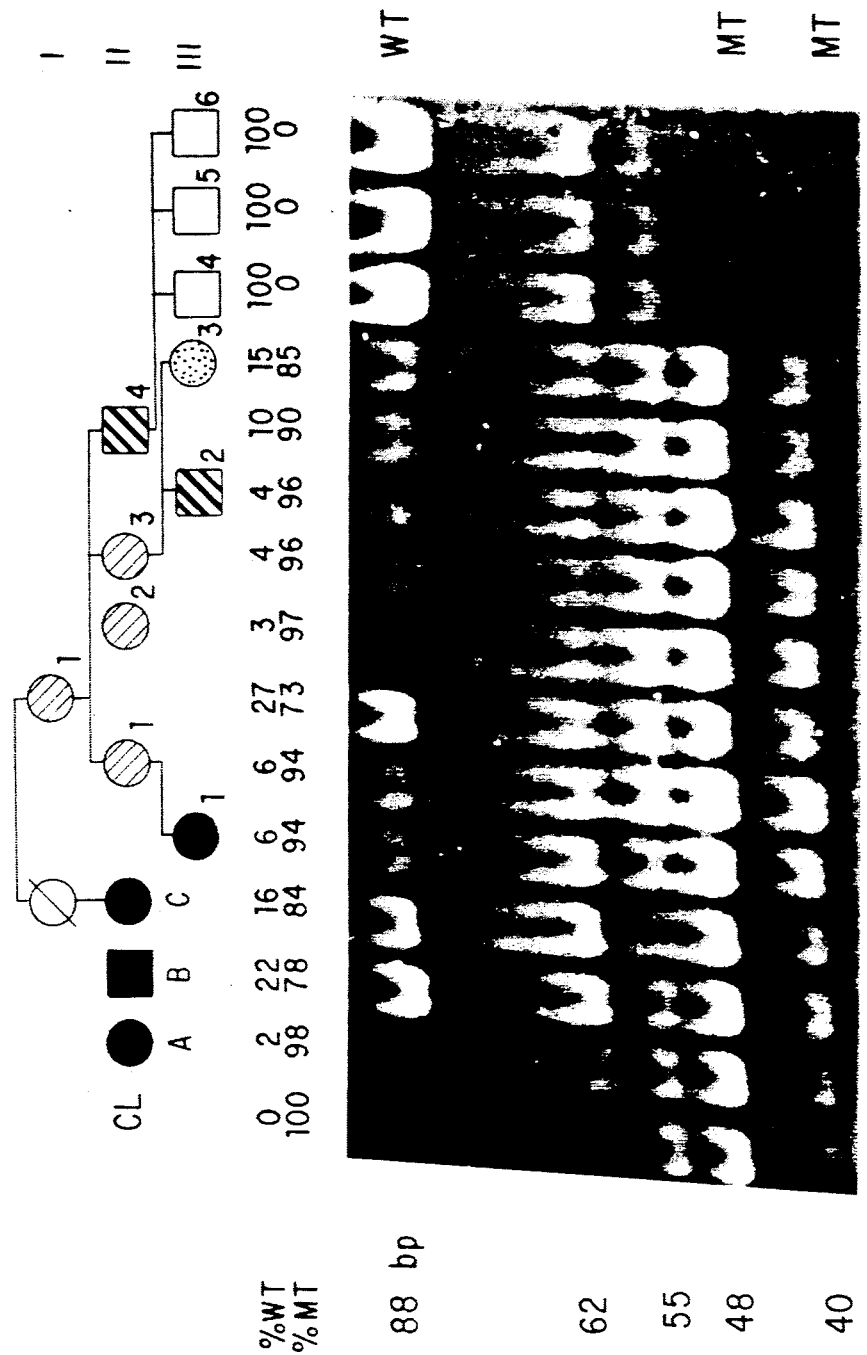
FIG. 1 shows the relative amounts of wild type and mutant mtDNA determined from analysis of CviJI digestion of mtDNA in MERRF probands and their maternal and paternal lineage relatives.

FIG. 1 shows the detection of the tRNA$^{Lys}$ np 8344 mutation by CviJI digestion in MERRF probands and their maternal and paternal lineage relatives. In FIG. 1, like symbols identify individuals with similar phenotypes. Group 1, including A (case III proband), B (case II proband), C, and III-1 (case I proband), had myoclonus and mitochondrial myopathy; Group 2, including I-1 and II 1-3, had EEG and VER aberrations, hearing loss and mitochondrial myopathy; Group 3, including II-4 and III-2, had EEG and VER aberrations and mitochondrial myopathy; Group 4, including III-3, had only mild EEG and VER aberrations; and Group 5, including III 4-6, had no clinical manifestations. In FIG. 1, CL indicates a mutant clone from the Case I proband whereas WT indicates wild type fragments and MT indicates mutant fragments.

Three independent MERRF cases were examined. Case I (III-1, FIG. 1) was the proband of a large maternal pedigree (Rosing et al., *Ann. Neurol.*, 17:228-237 (1985)), with primary respiratory Complex I and IV deficiencies (Wallace et al., *Cell*, 55:601-610 (1988)). She began to experience spontaneous myoclonic jerking in her mid-teens and progressed over ten years to include debilitating myoclonus, mitochondrial myopathy with ragged-red fibers and abnormal mitochondria, neurosensory hearing loss, dementia, hypoventilation and mild cardiomyopathy. Eight maternal lineage relatives with varying clinical manifestations were also examined, as shown in FIG. 1. The clinical characteristics of the pedigree are as follows: the proband's mother (II-1), grandmother (I-1) and maternal aunts (II-2, II-3) had cortical excitability detected by enhanced photic response on EEG and increased VER amplitudes, mitochondrial myopathy, and hearing loss; her maternal uncle (II-4) and cousin (III-2) had mild EEG aberrations and mitochondrial myopathy; her cousin (III-3) had mild EEG aberrations, but a normal muscle biopsy; her mother's cousin (C) had generalized myoclonus, mitochondrial myopathy, migraine headaches associated with occasional facial numbness; and her three paternal cousins (III-4, III-5, III-6) were normal.

Case II (B, FIG. 1) was an isolated male manifesting spontaneous myoclonus, first observed in his early 30s, mitochondrial myopathy, mild ataxia and a single episode of status epilepticus. His muscle mitochondria has 4% Complex I, 0.4% Complex I+III, 2% Complex IV, 6% Complex II+III and 44% Complex III specific activities relative to normal controls.

Case III (A, FIG. 1) was an isolated female who presented mild action myoclonus, mitochondrial myopathy, and mild proximal muscle weakness at 13 years of age.

Figure 2:
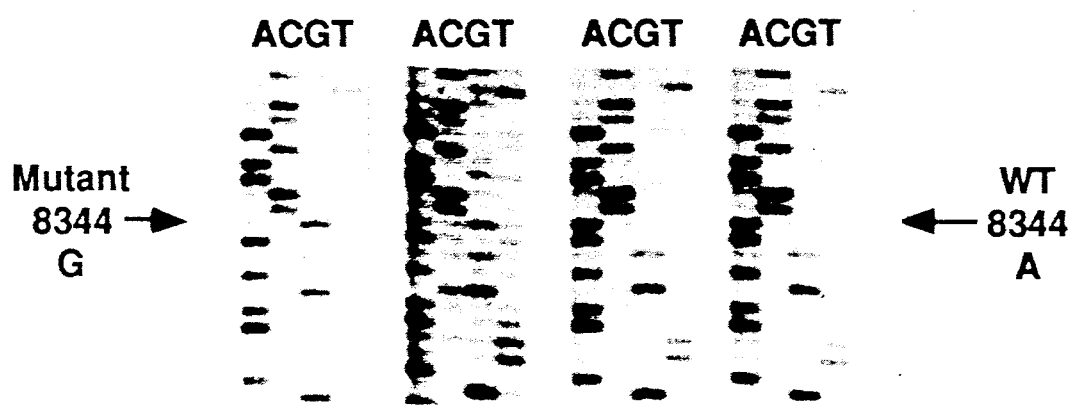
FIG. 2 shows the detection of the tRNA$^{Lys}$ np 8344 mutation by comparison of direct sequencing of the tRNA$^{Lys}$ sequence for individuals with MERRF (III-1) and mildly affected maternal relatives (III-3) as compared to individuals without the disease (MELAS-1 and MELAS-1).
Figure 3:
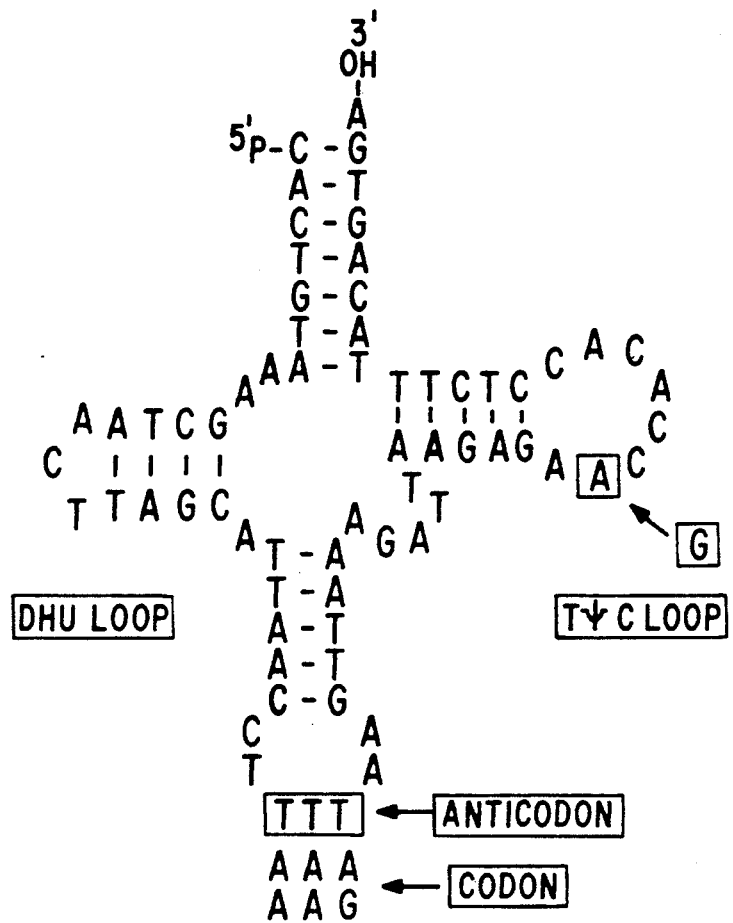
FIG. 3 depicts the proposed tRNA$^{Lys}$ structure showing the A to G mutation at np 8344.

The mtDNA of the Case I proband (III-1) was PCR amplified and sequenced directly. Ninety-four percent of the protein and structural RNA gene sequences and 57% of the D-loop sequences were surveyed. Only two mutations which altered conserved gene products were identified as described below. Of these, an A to G transition mutation at np 8344, as shown in FIG. 2, met all of the criteria expected for the MERRF mutation. This mutation altered the TΨC arm of the tRNA$^{Lys}$ gene, as shown in FIG. 3, and was confirmed by cloning the tRNA$^{Lys}$ gene into M13mp18 and sequencing two independent clones.

To determine if this mutation was specific for MERRF, this same region was sequenced from a second MERRF patient (Case II), two MELAS (Mitochondrial Encephalomyopathy, Lactic-acidosis and Stroke-like symptoms) patients, two CEOP (chronic external ophthalmoplegia plus) patients and 15 additional controls including AfroAmericans, Caucasians, Asians and Amerindians. The Case II proband had the same G substitution at position 8344, but all of the controls, the two MELAS patients, as shown in FIG. 2, and the two CEOP patients had the wild type A.

To determine the functional significance of the 8344 np substitution, the human tRNA$^{Lys}$ gene sequence was compared with that of a cow (Anderson et al., Nature, 290:457-465 (1982)) and mouse (Bibb et al., Cell, 26:167-180 (1981)). Surprisingly, the equivalent base was absent in the tRNA$^{Lys}$ genes of these species. To further clarify the phylogenetic significance of the 8344 np position, the region surrounding np 8344 from an orangutan mtDNA was sequenced. An A was present in the equivalent position in this species. Further studies show that the position is conserved also in the mouse, rat, hamster, chicken, xenopus, and cod. Therefore, substitution of the 8344 np A with a G in human mtDNA probably reduces tRNA efficiency but does not eliminate its function.

To extend the analysis to additional patients and controls, the restriction endonuclease CviJI (Xia et al., Nucl. Acids Res., 15:6075-6090 (1987)) was utilized. This enzyme cuts at the mutant sequence (AGCC) but not the wild type (AACC). A 183 np PCR fragment flanking the polymorphic site was prepared and digested with the enzyme. PCR fragments from samples with wild type mtDNA gave an 88 np fragment (FIG. 1, three rightmost lanes), while cloned mutant mtDNA gave 48 and 40 np fragments (FIG. 1, left lane). Both mtDNAs gave 62, 55, 12, 11 and 10 np fragments, of which the latter three migrated off the gel. The 55 np fragment is derived from the 63 np fragment by an as yet uncharacterized star activity as discussed below.

Using this test, all three MERRF probands were shown to have the mutation (FIG. 1) while 56 additional controls lacked the mutation. Thus, there is a perfect correlation between this mutation and MERRF with all three MERRF patients having the mutation and a total of 75 controls (41 Caucasians, 13 AfroAmericans, 21 Orientals) lacking the mutation.

2. The tRNA$^{Lys}$ Mutation is Heteroplasmic

The tRNA$^{Lys}$ gene was sequenced from several less affected maternal relatives of Case I. While all MERRF relatives had predominantly the mutant G at np 8344, some also had the wild type A. This sequence heteroplasmy is shown for III-3, the least affected maternal relative of the Case I proband (FIG. 2).

Heteroplasmy was confirmed by CviJI digestion of mtDNA from two of the MERRF probands as well as the maternal lineage relatives of Case I, as shown in FIG. 1. All of these individuals gave predominantly the mutant 48+40 np fragments. However, the Case II (B) and Case I (III-1) probands and all of the Case I maternal relatives also had varying amounts of the wild type 88 np fragment. By contrast, the Case III (A) proband had little, if any, of the wild type fragment and thus her muscle appears to be homoplasmic for the mutant mtDNA.

The proportion of mutant and wild type mtDNAs was quantitated by densitometric analysis of photographic negatives of the CviJI digest gels, as discussed below and shown in FIG. 1. These results were validated by comparison with a standard curve prepared by mixing the mutant and wild type mtDNA as discussed below. The Case III proband (A) had no detectable wild type mtDNA while the Case II proband (B) and the Case I maternal relatives C, I-1, II-4 and III-3 all had significant quantities of wild type mtDNA.

Figure 4A:
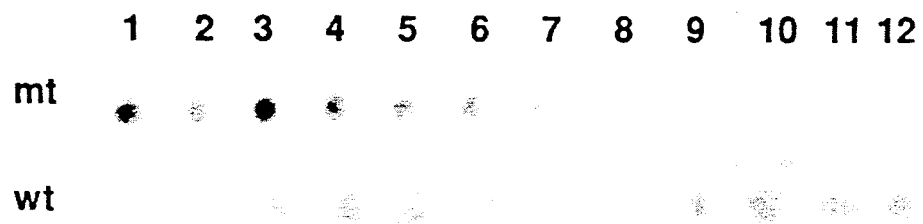
FIG. 4A shows alkaline dot blots of patient and control DNA fragments encompassing the np 8344 position hybridized to oligonucleotide probes homologous to the mutant and wild type mtDNA.

The presence of heteroplasmy in the MERRF patients was further confirmed by differential oligonucleotide hybridization of dot blots, as shown in FIG. 4. Alkaline dot blots (Farr et al., Proc. Natl. Acad. Sci. USA, 85:1629-1533 (1988)) were prepared using fragments encompassing the np 8344 mutation from six Case I maternal relatives (III-1, II-1, II-2, I-1, II-4 and III-3), the Case II (B) and Case III (A) probands and four controls. FIG. 4A shows the hybridization of mutant (mt) and wild type (wt) probes to duplicate spots of patient and control mtDNA PCR fragments. Spots 1-6 are MERRF Case I pedigree individuals III-1, II-1, II-2, I-1, II-4 and III-3. Spot 7, case II proband; 8, Case III proband; 9 and 12, Caucasian controls; 10, AfroAmerican control; and 11, Oriental control. Each spot contains approximately 200 ng (0.11 picomole) of a 2806 np PCR fragment.

Figure 4B:
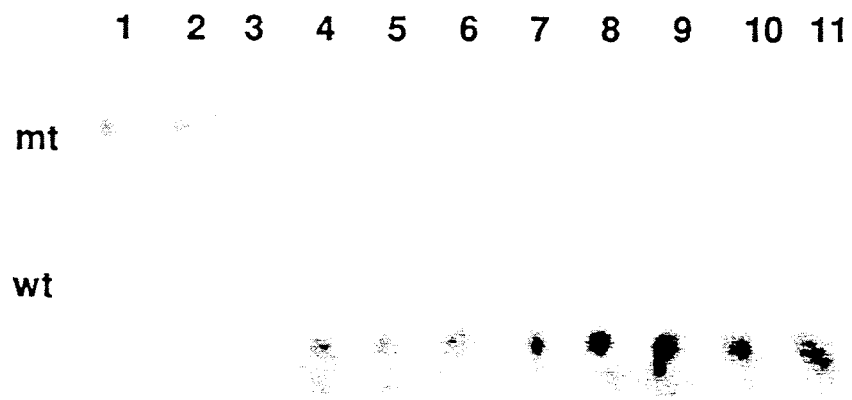
FIG. 4B shows the hybridization of mutant and wild type probes to varying concentrations of MERRF clone (1547 np) and control (2806 np) PCR fragments.

FIG. 4B shows the hybridization of mutant and wild type probes to varying concentrations of MERRF clone (1547 np) and control (2806 np) PCR fragments. MERRF clone DNA concentrations (rows 1 and 3) in picomoles are: lane 1) 0.196; 2) 0.171; 3) 0.147; 4) 0.122; 5) 0.107; 6) 0.098; 7) 0.073; 8) 0.049; 9) 0.024; 10) 0.009; 11) blank. Control PCR DNA concentrations (rows 2 and 4) in picomoles are: lane 1) blank; 2) 0.005; 3) 0.0135; 4) 0.027; 5) 0.040; 6) 0.054; 7) 0.059; 8) 0.067; 9) 0.081; 10) 0.095; 11) 0.108.

Hybridization intensities were compared to those obtained with known amounts of pure mutant and wild type mtDNAs. The two oligonucleotide probes, homologous to the mutant and wild type sequences as described below, specifically hybridized to the spots of their respective control DNAs (FIG. 4B). The mutant probe also hybridized to the mtDNA of all the probands and the Case I maternal relatives, but did not hybridize to the four controls (FIG. 4A). By contrast, the wild type probe hybridized most strongly to all four controls, less strongly to I-1 (dot 4) and II-4 (dot 5), even less strongly to III-3 (dot 6) and B (dot 7), least strongly to III-1 (dot 1), II-1 (dot 2) and II-2 (dot 3), and did not hybridize to proband A (dot 8). Hence there is an excellent correlation between the proportion of mutant and wild type mtDNAs detected by CviJI digestion and oligonucleotide hybridization.

3. Biochemical and Phenotypic Variation Correlates with MtDNA Genotype and Age

The biochemical and phenotypic variation previously described for the Case I pedigree (Wallace et al., *Cell*, 55:601–610 (1988)) was found to correlate with mtDNA genotype when patient age was controlled. It has been reported that respiration rates using NADH-linked substrates and succinate decline about two-fold from 20 to 90 years of age in normal individuals. A similar decline has been observed for cytochrome c oxidase and succinate-cytochrome c oxidoreductase (Complexes II+III), implying that respiratory decline is part of the normal aging process (Trounce et al., *The Lancet*, 637–639 (1989)). OXPHOS parameters were also observed to decline in the MERRF patients when grouped by mtDNA genotype. Individuals III-3, II-4 and I-1 who had similar genotypes (20–40% wild type mtDNA) but different ages (19, 50, 73 years) were compared. The anaerobic thresholds of these individuals were 1212, 1197 and 638 ml $O_2$/min; their specific activities for Complex I+III were 384, 168 and 30 nmol/min/mg; for Complex II+III were 1027, 656 and 474 nmol/min/mg; for Complex IV (sonicated mitochondria) were 1466, 966 and 591 nmol/min/mg; for Complex IV (freeze-thawed mitochondria) were 1203, 1053 and 609 nmol/min/mg; and their respiratory control ratios were 3.8, 2.6 and 2.2.

The effect of mtDNA genotype on biochemical defect became apparent when comparing individuals within a single generation and thus controlling for age as shown in Table I. For generation III, as the proportion of mutant mtDNAs increased, the OXPHOS parameters for (1) anaerobic threshold, (2) NADH-linked respiration rates, (3) Complex I (I and I+III) specific activity, (4) Complex IV specific activity in sonicated mitochondria, (5) respiratory control index, and (6) mitochondrial stability

TABLE 1

Association Between Biochemical Parameters and MtDNA Genotype

| COMPLEX | ASSAY | GENOTYPE CORRELATION Generation III | GENOTYPE CORRELATION Generation II + III |
|---|---|---|---|
| | EXERCISE | | |
| ANAEROBIC THRESHOLD | CALORIMETRY | 0.76 | 0.76 |
| | RESPIRATION | | |
| I, III, IV | M + G | 0.92 | 0.91 |
| II, III, IV | SUCCINATE | 0.53 | 0.28 |
| IV | ASC + TMPD | 0.67 | 0.77 |
| V | RCR | 0.56 | 0.67 |
| | ENZYMOLOGY | | |
| I | NADH-DB | 0.64 | 0.56 |
| I + III | NADH-CYT C | 0.65 | 0.64 |
| II + III | SUCC-CYT C | 0.51 | 0.33 |
| III | DBH$_2$-CYT C | 0.17 | 0.07 |
| IV | CYT C OXIDASE | | |
| | NONSONICATED | 0.13 | 0.11 |
| | SONICATED | 0.77 | 0.77 |
| | FRAGILITY INDEX | 0.84 | 0.83 |
| V | F1 ATP SYNTHASE | 0.64 | 0.53 |

ABBREVIATIONS:
CALORIMETRY = Indirect Calorimetry during exercise stress
M + G = malate + glutamate, ASC = ascorbate, TMPD = tetramethylphenylenediamine, RCR = respiratory control ratio;
NADH + DB = NADH-n-decyl coenzyme Q oxidoreductase;
NADH-cytc = NADH-cytochrome c oxidoreductase (rotenone-sensitive fraction)
SUCC-cyt c = succinate-cytochrome C oxidoreductase;
F1 ATP Synthase = activity in the F1 portion of the ATP synthase (represented by the Fragility Index) all declined. This effect is shown in Table 1 by correlation coefficients of 0.6 or better where individuals III-4, III-5, III-6 were included to provide the expected values for 100% normal mtDNA. A similar effect is seen in generation II as indicated by observing comparable correlation coefficients when their data was combined with generation III data. These results show a direct relationship between the tRNA$^{Lys}$ mutation and the MERRF mitochondrial OXPHOS defect and confirm that the primary effect of the tRNA$^{Lys}$ mutation is to reduce respiratory Complex I and IV stability and activity.

The effects of age and mtDNA genotype are also seen on clinical phenotype. For individuals III-3, II-4 and I-1, with similar proportions of normal mtDNAs, the phenotype is more severe in the older individuals. For individuals in generations II and III with similar ages, as the proportion of mutant mtDNAs increases, the severity of symptoms increases. For example, individual II-4 with 21% normal mtDNAs had less severe symptoms than individuals II-3, II-2 and II-1, who have 5 to 12% normal mtDNAs. Similarly, individual III-3 with 26% normal mtDNAs had only very mild clinical manifestations while individuals III-2 and III-1, with 5 and 13% normal mtDNAs, had more severe symptoms.

The relationship between mtDNA genotype, age and phenotype can also partially explain the differences between the MERRF probands. Case III (A) had no normal mtDNAs and showed symptoms in her early teens. Case I (III-1) had 13% normal mtDNAs and started to express symptoms in her late teens. Case II (B) and C had 30–40% normal mtDNAs and first showed symptoms at age 25–35 years.

4. DNA Preparation

Mitochondrial DNA can be derived from any cell from the patient by various methods; thus, mtDNA can be isolated from a variety of biological samples. For instance, a samll platelet pellet can be placed in distilled water and heated to boiling to release the mtDNA. Alternatively, blood can be fractionated on Ficoll-Hypaque gradients (Pharmacia, Piscataway, N.J.) followed by transforming the lymphocytes with Epstein-Barr virus as disclosed in *Am. J. Hum. Genet.* 38:461 (1986). Purified mtDNA can be obtained from these cells by enriching whole-cell lysates through precipitation of the chromatin with 1M NaCl. The mtDNA-rich supernatant can be further purified by proteinase digestion and organic extraction as disclosed in *Somat. Cell Mol. Genet.*, 12:41 (1986). Alternatively, mtDNAs can be purified from isolated mitochondria by detergent lysis and separation with the use of two density-gradient centrifugations with a cesium-chloride-ethidium bromide solution.

The following procedures work well for muscle DNA. For large preparations, DNA was extracted with selective enrichment for mtDNA as previously described (Wallace et al., *Cell*, 55:601-610 (1988)). Alternatively, 50-100 mg of muscle or mitochondria was homogenized, lysed with 0.5% SDS in 25 mM Tris and 1 mM EDTA and digested overnight with 0.5 µg/µl Protease K at 55° C. Protease K was heat inactivated, RNA digested with 1 µg/µl RNAse A, and the DNA purified using an affinity adsorption column (Qiagen, Studio City, Calif.).

The following procedure works well for 50 µl whole blood (collected in sodium heparin, EDTA, acid citrate dextrose, or lithium heparin), platelets and lymphocytes left over from fractionation of whole blood, dried blood spots, hair roots, fibroblasts, homogenized brain, homogenized muscle, and amniocytes. Dried blood spots on filter paper, such as Guthrie spots, may be used in this procedure by adding 190 µl of doubly-distilled H₂O to the paper folded up in a 1.5 mt centrifuge tube. Similarly, 3-4 plucked hairs may be used. With such extremely limited samples, 25-50% of the DNA recovered should be used in a PCR reaction. When starting with as little as 50-190 µl of whole blood, however, 5 µl of the final suspension is adequate for amplification in a MERRF diagnostic test.

Doubly-distilled water is added to the sample to bring the volume to 190 µl. 200 µl 50 mM Tris, 2 mM EDTA, 1% SDS lysis buffer are added. Following the addition of 10 µl of 10 mg/ml Protease K, the sample is incubated at 55° C. overnight (or for at least 2 hours). The sample is incubated at 93°-95° C. for 10 minutes to inactivate the Protease K. 100 µl of 2 mg/ml RNAse A (can use 120 µg minimun) is added and the sample is incubated for 5 minutes at room temperature. Following the addition of 100 µl 600 mM NaOH, the sample is inverted to mix. 300 µl of 2.55M potassium acetate, pH 4.8, is then added. The mixture is spun for 15 minutes at 4° C. The supernatant can be further purified by either phenol extraction and alcohol precipitation, as described below, or Geneclean (adsorption matrix manufactured by BIO 101, LaJolla, Calif.) or Qiagen tip 20 (DNA anion exchange resin, made by QIAGEN, Inc., Studio City, Calif.).

The phenol extraction consists of adding a volume of phenol/chloroform equal to the supernatant volume and extracting the proteins by vortexing or shaking the tube followed by spinning for 5 minutes. The supernatant is transferred to a Centricon-100 (Amicon, Danvers, Mass.), the volume is brought up to 2 ml with doubly-distilled water, and the supernatant is spun at 3000 rpm for 30-40 minutes. After the filtrate is discarded, the Centricon-100 unit is inverted into a retentate cup and spun at 2000 rpm for 10-15 minutes to recover the DNA in about 40 µl. The procedures involving the Centricon-100 are repeated 2 more times.

Alternatively, instead of utilizing the Centricon-100 procedures, the supernatant can be transferred to a new tube and two volumes of 100% ETOH added. Following mixing, the mixture is allowed to precipitate at −20° or −80° C. for 1 hour. The mixture is spun in the cold for 30 minutes and the supernatant is poured off. 70% ETOH is added, the cap is closed, and the tube is inverted several times. Following a 10 minute spin in the cold, the supernatant is poured off and the pellet is dried in a speed vacuum for approximately 10-15 minutes.

5. DNA Sequencing

The mtDNA was sequenced directly using asymmetrically amplified mtDNA templates, 7-deaza-2'-deoxyguanosine 5'-triphosphate and Taq polymerase (Shoffner et al., *Proc. Natl. Acad. Sci. USA*, 86:7952-7956 (1989); Innis et al., *Proc. Natl. Acad. Sci. USA*, 85:9436-9440 (1988)). Asymmetrically amplified DNA was prepared from 18 overlapping double stranded PCR fragments with the following nucleotide position (np) coordinates (Anderson et al., *Nature*, 290:457-465 (1981)): 534-1696, 1562-3717, 2772-4508, 3007-4508, 3598-5917, 3951-5917, 5317-7608, 5702-7608, 7392-8628, 8282-10107, 9911-12576, 9911-11873, 10714-12576, 11711-14208, 13914-15865, 14728-725, 15243-725, 11673-16547. All synthetic oligonucleotides (Microchemical Facility for Molecular Biology, Emory University) were used as supplied without further purification. Sequencing primers were prepared approximately every 300 np and the regions sequences were np 316-432, 593-1149, 1390-1902, 2056-2190, 2328-9617, 9672-13217, 13246-14458, 14784-16121, 16381-220. Nucleotide substitutions relative to the Cambridge sequence (Anderson et al.) which would alter gene products occurred at np 750 in the 12S rRNA gene (A to G), np 2706 in 16S rRNA (A to G), np 4769 in ND2 (A to G), np 8344 in tRNA$^{Lys}$ (A to G), np 8860 in ATP6 (A to G), np 13702 in ND5 (G to C) and 15326 in cytb (A to G). Mutations at np 2706, 4769, 8860, 13702 and 15326 were excluded because they were also found in LHON and/or other human mtDNA sequences (Wallace et al, *Science*, 242:1427-1430 (1988) and were not associated with conserved gene products in cow or mouse (Anderson et al., Bibb et al., *Cell*, 26:167-180 (1981)). Only mutations at np 750 and 8344 remained candidates for the MERRF mutation.

The human mtDNa tRNA$^{Lys}$ gene was amplified for sequencing using a forward (→) primer at 6449-6465 and a reverse (←) primer at 9244-9225. Single stranded template was generated from this fragment with 7392-7410→ and ←8608-8628 primers at a 1:100 ratio. The orangutan mtDNA tRNA$^{Lys}$ gene was amplified using primers from the human sequence at 6795-6811→ and ←9154-9172 and single stranded template prepared with primers 7392-7410→ and ←8902-8921 at a 1:100 ratio. The sequence was read from primer 8150-8166→ by annealing and labeling at 51° C. for 10 minutes and 3 minutes, respectively, with dideoxy termination reactions performed at 70° C. for 5 minutes followed by 24° C. for 12 minutes (Shoffner et al., *Proc. Natl. Acad. Sci. USA*, 86:7952-7956 (1989)).

The region surrounding mtDNA tRNA$^{Lys}$ was cloned using a PCR fragment, (PstI)-7392-7410→ to ←-8902-8921-(HindIII). The fragment was directionally inserted into M13mp18 and sequenced.

6. CviJI Digestion

The tRNA$^{Lys}$ gene region surrounding the 8344 mutation site was amplified as a 183 np fragment containing the mtDNA bases 8282-8438 and a 26 np tail extending from np 8438 using primers 5'-CCCCTCTAGAGC-CCACTGTAAAGC→ and ←-GGAATGT-GATAAGGAGTAGTGGG-(CACGCGCCGCGCCGCCGACCGCCGCC)-5'.

The DNA fragments were purified using Centricon 30 columns (Amicon, Danvers, Mass.). Approximately 360 ng of PCR product were digested with 2-3 U of CviJI (PuGCPy) (obtained from Dr. James L. Van Etten, Department of Plant Pathology, University of Nebraska, Lincoln, Nebr.) for 5.5 hours (Xia et al., *Nucl. Acids Res.*, 15:6075-6090 (1987)) and the fragments resolved on 8% polyacrylamide gels in 10 mM Tris, 10 mM Borate, 2.5 mM EDTA, pH 8.3. The fragments generated by wild type mtDNa were 88, 62, 12, 11 and 10 np. Those from mutant mtDNA were 62, 48, 40, 12, 11, and 10 np. Incubation times necessary to yield complete digestion produced a star activity that cut the non-polymorphic 62 np fragment to approximately 55 np. The best candidate for this additional cleavage site is in the tail of the reverse primer at a degenerate site (GGCG) 8 np from position 8438. Alternatively, this cleavage could be the result of an oligonucleotide synthesis error creating a recognition sequence (PuGCPy).

The proportion of mutant and wild type mtDNAs was calculated from densitometry of photographic negatives using and UltroScan XL Laser Densitometer equipped with version 2.0 of the Gel-Scan XL software package (Pharmacia LKB Biotechnology, Piscataway, N.J.). The relative number of molecules (N) for the 88 np fragment (N$_{88}$) and 48+40 np fragment (N$_{48+40}$) were calculated by N$_{88}$=A$_{88}$/88 and N$_{48+40}$=A$_{40+48}$/88, where A is the area under the polymorphic peak. The proportion (P) of wild type (WT) and mutant (MT) mtDNAs was calculated as $$P_{WT}=N_{88}/N_{88}+N_{48+40} \text{ and}$$
$$P_{MT}=N_{48+40}/N_{88}+N_{48+40}.$$

Standards prepared with 360 ng of pure wild type mtDNA and cloned mutant mtDNA in the proportions of 100%:0%, 75%:25%, 50%:50%, 25%:75% and 0%:100% gave densitometric values of 99%:1%, 62%:38%, 40%:60%, 27%:73%, and 0%:100%, respectively.

7. Differential Oligonucleotide Hybridization

Mutant and wild type mtDNAs were quantitated by differential oligonucleotide hybridization. The wild type probe, 5'-GATTAAGAGAACCAACACC, was hybridized at 38° C. and washed at 42° C. The mutant probe, 5'-GGTGTTGGCTCTCTTAATC, was hybridized at 42° C. and washed at 44° C. DNAs were loaded onto filters using the alkaline dot blot procedure (Farr et al., *Proc. Natl. Acad. Sci. USA*, 85:1629-1633 (1988)). Triplicate spots containing 200 ng of a 2806 np PCR fragment (np 6449-9244+a 10 np tail) were loaded for each patient and control individual. Standard curves were prepared with duplicate spots of DNA ranging from 200 to 0 ng, the wild type prepared from the 2806 np fragment and the mutant from a 1642 np fragment amplified from the M13mp18 mutant clone using standard forward and reverse M13 sequencing primers. Filters were hybridized with the mutant probe, autoradiographed, stripped with 0.1M NaOH and rehybridized with the wild type probe. The relative number of moles of the mutant and wild type mtDNAs in each sample was estimated by comparing the average spot intensity for each probe with the values from the standard curves.

8. Discussion

Six lines of evidence indicate that the tRNA$^{Lys}$ mutation at np 8344 is the cause of MERRF. First, it is one of only two mutations identified in the MERRF mtDNA which altered conserved elements of gene products. Second, it correlates perfectly with the disease; three independent patients but no controls have the mutation. Third, it alters a mtDNA tRNA which would inhibit mitochondrial protein synthesis and thus account for the reduction observed in the synthesis of the larger mitochondrial translation products. Fourth, it alters an A found in the tRNA$^{Lys}$ that appears to be conserved in higher primates. Fifth, it is heteroplasmic, consistent with a recent origin for a deleterious mtDNA mutation. Sixth, the proportion of mutant mtDNAs correlates with the severity of the symptoms and the extent of the respiratory Complex I and IV deficiencies when controlling for age. Thus, tRNA$^{Lys}$ mutation has all of the characteristics predicted for the MERRF mutation and hence must be the cause of the disease.

While this mutation is deleterious, it probably does not completely eliminate tRNA$^{Lys}$ function. This is apparent since the Case III proband is essentially homoplasmic, yet she did not manifest overt symptoms until her early teenage years. If this is the case, even small amounts of normal mtDNA may be sufficient to partially offset major symptoms.

The effect of age on expression of the mutant phenotype may provide insight into the progression of OXPHOS diseases. Patients born with mutant mtDNA would start with a lower mitochondrial OXPHOS level than individuals born with a normal genotype. Hence, as their residual OXPHOS capacity declines with age, it would traverse organ-specific energetic thresholds much earlier than would otherwise occur. Residual muscle mitochondrial OXPHOS activity, therefore, should give the best correlation with current clinical phenotype (Wallace et al., *Cell*, 55:601-510 (1988)), but mtDNA genotype should provide a better indication of the age related prognosis.

While variation in mtDNA genotype and age can account for much of the variation observed in the MERRF patients and their maternal relatives, it does not account for all of the clinical differences. Additional factors that could affect phenotype variation might be other nuclear genetic factors, environmental factors and somatic replicative segregation. This latter factor may be of considerable importance since in studies on heteroplasmy in Leber's Hereditary Optic Neuropathy patients, different somatic tissues can differ markedly in the percentage of mutant mtDNAs. For example in some patients, blood can be predominantly mutant while hair can be predominantly wild type. Thus, the same average mtDNA genotype could result in very different organ-specific genotypes and hence, clinical phenotypes.

Identification of the MERRF mutation provides the final element necessary for our understanding of mtDNA genetic diseases. The maternal inheritance of the mtDNA imparts a maternal predisposition to the disease. The meiotic and mitotic segregation of the heteroplasmic mtDNA mutation results in variable OXPHOS deficiencies between patients and within patients. The defective mtDNAs reduce the mitochondrial ATP generating capacity of the patient's organs which then become affected when the decline of their mitochondrial ATP generating capacity falls below the minimum necessary for normal tissue function.

The demonstration that MERRF is due to a tRNA$^{Lys}$ mutation provides the first evidence that a defect in protein synthesis can case a genetic disease. It also demonstrates that certain forms of epilepsy are due to deficiencies in mitochondrial OXPHOS. The development of simple assay techniques for the MERRF mutation together with the elucidation of the relationship between heteroplasmic mtDNA, age and the patient phenotype, should greatly enhance the ease and accuracy of diagnosis and counseling of this devastating disease.

What is claimed is:

1. A method of detecting neuromuscular disease in a patient, comprising the step of ascertaining the presence of a transition mutation at the nucleotide position 8344 of human mitochondrial DNA obtained from a biological sample from said patient.

2. The method of claim 1, wherein said neuromuscular disease is Myoclonic Epilepsy and Ragged Red Fiber disease.

3. The method of claim 1, wherein said transition mutation causes said neuromuscular disease.

4. The method of claim 1, wherein said transition mutation is associated with said neuromuscular disease as a risk factor.

5. The method of claim 1, wherein said biological sample contains a cell from said patient.

6. The method of claim 5, wherein said cell is selected from the group consisting of a blood cell, blood platelet, white blood cell, transformed lymphoblast, hair follicle cell, epidermal cell, urinary tract cell, cerebrospinal fluid cell, chorionic villae cell, muscle cell, brain cell, liver cell, kidney cell, heart cell, and amniocentesis fluid cell.

7. The method of claim 1, wherein said transition mutation changes an adenine to guanine at said 8344 position.

8. The method of claim 1, wherein said transition mutation alters the TΨC loop of the tRNA$^{Lys}$ gene.

9. The method of claim 1, wherein said transition mutation oreates an endonuclease restriction site.

10. The method of claim 9, wherein said endonuclease is CviJI.

11. The method of claim 1, wherein said ascertaining step is accomplished according to the steps of:
 (a) obtaining mitochondrial DNA from said sample;
 (b) digesting said mitochondrial DNA with a restriction endonuclease;
 (c) separating the resulting mitochondrial DNA fragments; and
 (d) determining the length of said fragments to detect the presence of said transition mutation at said 8344 position.

12. The method of claim 11, wherein said mitochondrial DNA from said sample is selected from the group consisting of crude complete DNA, purified complete DNA, amplified complete DNA, crude partial DNA, purified partial DNA, and amplified partial DNA.

13. The method of claim 11, wherein said endonuclease is CviJI.

14. The method of claim 11, wherein said separating step is selected from the group consisting of agarose electrophoresis followed by Southern blotting, end-labeling said fragments followed by polyacrylamide gel electrophoresis, development of the digested products on agarose gels following amplification and digestion of said mitochondrial DNA, and development of the digested products on polyacrylamide gels following amplification and digestion of said mitochondrial DNA.

15. The method of claim 1, wherein said ascertaining step is accomplished according to the steps of:
 (a) obtaining mitochondrial DNA from said sample;
 (b) obtaining a differential hybridization oligonucleotide probe that is complementary to the nucleotide sequence of one strand of test mitochondrial DNA in the region surrounding said nucleotide position 8344;
 (c) hybridizing said probe with said mitochondrial DNA from said patient; and
 (d) determining the extent of said hybridization to detect the presence of said transition mutation at said 8344 position.

16. The method of claim 15, wherein said test mitochondrial DNA is wild type mitochondrial DNA.

17. The method of claim 15, wherein said test mitochondrial DNA is mutant mitochondrial DNA that possess a guanine at said 8344 position.

18. The method of claim 15, wherein said probe ranges from 17 to 23 nucleotide units in length.

19. The method of claim 15, wherein said probe has the nucleotide sequence 5'-GATTAAGAGAAC-CAACACC such that nucleotide A at position 8344 is said differential nucleotide.

20. The method of claim 15, wherein said probe has the nucleotide sequence 5'-GGTGTTGGCTCTCTTAATC such that nucleotide C at position 8344 is said differential nucleotide.

21. The method of claim 15, wherein said mitochondrial DNA from said sample is selected from the group consisting of crude complete DNA, purified complete DNA, amplified complete DNA, crude partial DNA, purified partial DNA, and amplified partial DNA.

22. The method of claim 1, wherein said ascertaining step is accomplished according to the steps of:
 (a) obtaining mitochondrial DNA from said sample;
 (b) amplifying a region of said mitochondrial DNA surrounding said 8344 position; and
 (c) sequencing said amplified mitochondrial DNA to determine the identity of the nucleotide at said 8344 position.

23. The method of claim 22, wherein said mitochondrial DNA from said sample is selected from the group consisting of crude complete DNA, purified complete DNA, crude partial DNA, and purified partial DNA.

24. The method of claim 1, wherein said ascertaining step is accomplished according to the steps of:
 (a) obtaining mitochondrial DNA from said sample;
 (b) preparing a DNA fragment containing the 8344 nucleotide position;
 (c) developing said fragment by electrophoresis on a polyacrylamide gel containing a denaturant; and (d) detecting said mutation by the altered mobility of said fragment containing said mutation.

25. A method of detecting neuromuscular disease in a patient, comprising the step of ascertaining the presence of a transition mutation at the nucleotide position 8344 of human mitochondrial DNA obtained from a biological sample from said patient, wherein said ascertaining step is accomplished according to the steps of:

(a) obtaining mitochondrial DNA from said sample;
(b) digesting said mitochondrial DNA with a restriction endonuclease;
(c) separating the resulting mitochondrial DNA fragments; and
(d) determining the length of said fragments to detect the presence of said transition mutation at said 8344 position.

* * * * *